United States Patent [19]

Swetly et al.

[11] 4,266,024

[45] May 5, 1981

[54] PROCESS FOR THE PRODUCTION OF HUMAN INTERFERON

[75] Inventors: Peter Swetly; Günther R. Adolf; Gerhard Bodo, all of Vienna; Silvia J. Lindner-Frimmel, Perchtoldsdorf; Peter Meindl; Hans Tuppy, both of Vienna, all of Austria

[73] Assignee: Boehringer Ingelheim GmbH, Ingelheim am Rhein, Fed. Rep. of Germany

[21] Appl. No.: 38,787

[22] Filed: May 14, 1979

[30] Foreign Application Priority Data

May 17, 1978 [DE] Fed. Rep. of Germany ....... 2821466
Feb. 17, 1979 [DE] Fed. Rep. of Germany ....... 2906160

[51] Int. Cl.³ .............................................. C12P 21/00
[52] U.S. Cl. ..................................... 435/68; 424/85; 435/811; 260/112 R
[58] Field of Search ................. 424/85; 435/236, 237, 435/238, 68; 260/112 R; Dig. 814

[56] References Cited

U.S. PATENT DOCUMENTS 3,773,924  11/1973  Ho et al. ................................ 424/85

FOREIGN PATENT DOCUMENTS 520  2/1979  European Pat. Off. ................... 424/85

OTHER PUBLICATIONS

Yoshida et al., Chemical Abstracts, vol. 89, 88741p (1978).
Pakidysheva et al., Chemical Abstracts, vol. 81, 149946t (1974).
Mecs et al., Chemical Abstracts, vol. 80, 78638k (1974).
Berthold et al., Chemical Abstracts, vol. 89, 105634a (1978).

*Primary Examiner*—Delbert R. Phillips
*Assistant Examiner*—Blondel Hazel
*Attorney, Agent, or Firm*—Hammond & Littell, Weissenberger & Muserlian

[57] ABSTRACT

This invention is directed to a process of producing interferon which comprises incubating permanent cell lines of lymphoblast origin or human fibroblast cells with interferon inducers and stimulator substances and recovering the interferon produced.

6 Claims, No Drawings

PROCESS FOR THE PRODUCTION OF HUMAN INTERFERON

FIELD OF THE INVENTION

This invention is directed to the preparation of interferon. More particularly, this invention is directed to an improved process for preparing interferon from permanent cell lines of lymphoblast origin or human fibroblast cells.

BACKGROUND OF THE INVENTION

The production of human interferon from cells of human origin has found worldwide attention because of its therapeutic potential as well as for the treatment of acute and chronic virus infections and for cancer therapy. The required amounts of interferon cannot be provided at the present time with established producers because conventional induction of tissue culture cells results in low concentrations of interferon.

The production of interferon according to already published procedures is conventionally achieved by adding interferon inducers such as, for example, a viral inducer or a nucleic acid inducer, to the culture medium of human cells. After this induction period, cells are removed from interferon containing cell supernatants and the remainder of the inducers is inactivated by the addition of mineral acid for several days. The crude interferon preparation obtained in that way can be concentrated and purified thereafter according to known methods. See, for example, German Published Application (DOS) No. 2,724,918.

OBJECTS OF THE INVENTION

It is an object of this invention to provide a process for producing interferon.

It is also an object of this invention to provide an improved process for producing interferon from permanent cell lines of lymphoblast origin or human fibroblast cells.

These and other objects will become more apparent in the discussion below.

DETAILED DESCRIPTION OF THE INVENTION

It has been surprisingly found that the addition of a stimulator substance to cell culture medium significantly increases the interferon production by a factor of from about four to sixty, as compared to production from cultures not exposed to stimulator substances. According to the invention, interferon is produced by incubating permanent cell lines of lymphoblast origin or human fibroblast cells with interferon inducers and stimulator substances and recovering the interferon produced.

The cells in which interferon is produced according to the invention are human cells. Human cells commonly used in this manner are either permanent cell lines of lymphoblast origin like Namalwa cells (see, G. Klein et al., Intern. J. Cancer, 10, 44–57 (1972)) or human fibroblast cells, either diploid with a restricted life span, or heteroploid with an infinite capacity for division.

The interferon inducers can be any of those known to be useful in this way. Inducing viruses are usually paramyxo viruses such as hemagglutinating virus Japan (HVJ=Sendai virus) or Newcastle disease virus; rhabdoviruses like vesicular stomatitis virus; measle viruses; or Reogroup viruses like reo virus or blue tongue virus. Nucleic acid inducers are usually double stranded ribonucleic acids like poly (I:C), either alone or in combination with metabolic inhibitors and/or polycations.

Useful stimulator substances include substances which, upon addition to the cell culture medium, increase the proportion of interferon-producing cells. More specifically, they are defined as substances which upon addition to the cell culture medium, result in the cells supported by this medium at optimal nutritional conditions, transgressing from an exponential growth phase to a resting stage. This resting stage corresponds according to the DNA (desoxyribonucleic acid-) content of the cells to a postmitotic stage (G1phase-like stage of the cell cycle) without DNA synthesis.

Substances which have proved especially valuable as stimulator substances include saturated aliphatic carboxylic acids such as alkanoic acids with from 3 to 6 carbon atoms, i.e., propionic acid, n-butyric acid, isobutyric acid, n-valeric acid, caproic acid, and their salts with inorganic or organic bases; N,N'-diacetylated diamines containing from 4 to 8 carbon atoms, especially the α, ω-derivatives such as pentamethylenebisacetamide, hexamethylenebisacetamide or heptamethylenebisacetamide; organic sulphur compounds, for example, sulfoxides such as dimethylsulfoxide; and glucocorticoids, which in 11β-position are substituted by a hydrophilic group such as a halogen atom, for example, a fluorine, chlorine, or bromine atom, a hydroxy or hydroxymethyl group such as, for example, hydrocortisone, dexamethasone, prednisolone, aldosterone, triamcinolone, or cortexolone. The end-concentration of these stimulators is approximately 0.01 μmoles to 300 m moles/l. The preferred end-concentration of an alkanoic acid used as stimulator is, however, 0.5 to 5 m moles/l; or a diacetylated diamine; 1 to 10 m moles/l; of an organic sulphur compound such as dimethylsulfoxide, 50 to 300 m moles/l, and of glucocorticoids, 0.01 to 10 μmoles/l.

Especially potent stimulator substances include propionic acid, n-butyric acid, n-valeric acid and their alkali salts, such as sodium salts, hexamethylenebisacetamide, dimethylsulfoxide, dexamethasone, triamcinolone, hydrocortisone, and prednisolone. The addition of stimulator substances is preferably prior to the interferon induction with interferon inducers; however, addition prior to and during the induction period can be applied. The increase in yield of interferon according to this invention is due both to an increase of the percentage of interferon producing cells and to an increase in interferon yield on a per cell basis.

The process of this invention is preferably carried out as follows:

Namalwa cells are cultivated in a growth medium, preferably the medium RPMI 1640 (Gibco Co., USA, or Flow Co., Great Britain), which contains the following substitutions: Tryptose phosphate broth (10 to 25% by volume, preferably however, 20% by volume); and partially purified human serum (1 to 10% by volume, preferably, however, 2 to 6% by volume). As an alternative to human serum, serum or serum fractions of other species can be applied such as fetal bovine serum at a concentration of from about 5 to 15% by volume.

To such a medium, which supports cell proliferation in suspension at a density of from 0.2 to $5 \times 10^6$ cells/ml, preferably, however, at a density of from 0.5 to $1 \times 10^6$ cells/ml, the stimulator substance (i.e., the sodium salt of n-butyric acid) is added at a concentration of preferably 1 m mol/l. Cells are further incubated at these conditions at a preferred temperature of from 35° to 37° C. for from 6 to 72 hours, preferably, however, for from 24 to 48 hours. After the stimulation period, cells are harvested, preferably by centrifugation, and resuspended at a density of approximately $50 \times 10^6$ cells/ml medium, with or without stimulator substance. To this suspension the interferon inducer, such as HVJ (Sendai virus) is added and incubated for approximately 1 to 3 hours. The thus induced cells are collected by centrifugation, resuspended at a density of from 5 to $10 \times 10^6$ cells/ml in a serum-free cell culture medium (Gibco Co., U.S.A., or Flow Co., Great Britain) such as in Eagle's Minimal Essential Medium, and further incubated at from 35° to 39° C. at a pH value of from 6.7 to 8.0, preferably 7.3, for a time span of from 15 to 24 hours, preferably from 18 to 20 hours, in the absence or in the presence of the stimulator substance. The such obtained suspension containing the crude lymphoblastoid interferon is separated from cells and cell debris by centrifugation. To inactivate residual inducer virus the supernatant is adjusted to a pH of 2.0 by addition of a mineral acid such as hydrochloric acid and incubated at from 0° to 4° C. for from 3 to 5 days.

The following recovery steps can be applied for the further purification, concentration and stabilization of the crude human lymphoblastoid interferon:

(a) The obtained solution is neutralized with, for example, sodium hydroxide, and interferon is precipitated from this solution by addition of a zinc salt such as zinc acetate and pelleted by centrifugation. The thus obtained pellet is solubilized in cold diluted hydrochloric acid such as 0.1 N hydrochloric acid.

(b) This solution is clarified by centrifugation and mixed with an ion exchanger, preferably SP-Sephadex C-25 (Pharmacia Fine Chemicals Uppsala, Sweden) and mechanically agitated for several hours.

After adsorption of the interferon to the ion exchanger, residual zinc ions are removed by repeated washings with a buffer solution, such as washing three times with 0.1 mol/l glycine/hydrochloric acid buffer solution having a pH of 2.5 followed by washing three times with a buffer solution containing 0.1 mol/l of potassium citrate and 0.005 mol/l of disodium ethylenediaminetetraacetate and having a pH of 4.0.

After these washing procedures, the ion exchanger, together with the adsorbed interferon, is suspended in the citrate buffer and transferred to a chromatographic column. Interferon is eluted from the ion exchanger in a moderate basic buffer solution such as a solution containing 0.1 mol/l of potassium phosphate and 1 mol/l of potassium chloride and having a pH of 8.0.

(c) The protein containing fractions of the eluate are collected at low temperature and adjusted to a pH of 3.5. After clarification by centrifugation, interferon is precipitated from the clear supernatant by addition of a potassium thiocyanate solution. The precipitate protein synthesis is allowed to settle, collected by centrifugation, dissolved in a small volume of a moderately basic buffer solution such as a solution containing 0.1 mol/l of potassium phosphate and having a pH of 8, and ultracentrifuged.

(d) The supernatant is further purified by column chromatography. Preferably useful is a molecular sieve such as Sephadex G-100 (Pharmacia Fine Chemicals, Uppsala, Sweden) with a particle size of 40 to 120 μm and an eluant containing phosphate buffered saline with 0.001 moles/l of disodium ethylenediaminetetraacetate. Before application of the interferon solution the column is usually standardized with proteins of known molecular weight. Those fractions of the eluates are then collected which correspond to proteins of a molecular weight in the range of 10,000 to 35,000 Daltons.

(e) The pooled fractions are adjusted with hydrochloric acid, preferably to a pH of 3, and applied to a small column containing an ion exchanger such as SP-Sephadex which had been prewashed with a solution containing 0.1 mol/l of potassium citrate and having a pH of 3.

At this pH interferon is adsorbed to the ion exchanger, from where it can be eluted after washing with citrate buffer in a phosphate buffer solution such as one containing 0.1 mol/l of potassium phosphate and having a pH of 8. The fractions containing protein are pooled and dialyzed against phosphate buffered saline.

EXAMPLES

The following examples are included for illustrative purposes only and are not intended to limit the scope of the invention.

Preparation of Namalwa Cells and Sendai Virus

Namalwa cells can be propagated in suspension culture in a fermentation vessel. The culture medium contains medium RPMI 1640 which is substituted with 20% by volume of tryptose phosphate broth and from 2 to 4% by volume of fractionated human serum. Fractionation of human serum is achieved by partial precipitation of serum proteins with 6% polyethylene glycol 6000 (see Inglot et al. in Acta Virol. 19, 250-254, 1975). The cells grow to densities of from 2 to $7 \times 10^6$ cells/ml.

Sendai virus (HVJ) is propagated in chicken embryos and purified by high speed centrifugation. Sendai virus is suspended in cell culture medium by sonication and stored at $-70°$ C.

EXAMPLE 1

Namalwa cells in a logarithmic growth phase were suspended in growth medium at a density of $5 \times 10^5$ cells/ml. To this cell suspension the stimulator substance was added for the time t hours at a concentration of c m moles/l at 37° C. During the period of exposure to the stimulator substance, the rate of cellular DNA synthesis was reduced to less than 2% of a control culture (without stimulator substance), and the cells entered a resting state which corresponded to the G1 phase of the cell cycle. After this treatment cells were collected by centrifugation ($700 \times g$, 15 minutes) and further incubated at a density of $5 \times 10^7$ cells/ml in 1.7 liter of growth medium at 37° C. for 2 hours in roller bottles together with $2^{10}$ hemagglutinating units HVJ/ml. Cells induced in this way were collected by centrifugation and further incubated at a density of $5 \times 10^6$ cells/ml in 17 liter serum free Eagle's Minimum essential medium (with Earle's salts) at 35.5° C. and a pH of 7.3 for 30 hours. For this step a 20 liter bottle with a mechanical stirring device was used. After pelleting of cellular material ($2000 \times g$, 30 minutes) the crude solution (i.e., cell supernatant) was adjusted to a pH of 2 with 5 N hydrochloric acid at a maximal temperature of 10° C. and stored at 4° C. for 3 to 5 days to inactivate the HVJ used for induction of interferon.

The following table demonstrates the obtained increase in interferon when n-butyric acid at a concentration of c m moles/l was added as stimulator substance:

TABLE 1.

| | Concentration of Stimulator Substance c (m moles/l) | Period of Pretreatment t (hours) | IU/$10^6$ cells+ | Yield Increase Factor |
|---|---|---|---|---|
| (a) | 0 | — | 280 | 1 |
|  | 1 | 26 | 7,270 | 26 |
| (b) | 0 | — | 1,480 | 1 |
|  | 2 | 40 | 55,550 | 38 |
| (c) | 0 | — | 1,100 | 1 |
|  | 1 | 48 | 36,000 | 33 |
|  | 2.5 | 48 | 65,520 | 60 |
| (d) | 0 | — | 1,630 | 1 |
|  | 1 | 68 | 44,000 | 27 |

+ International units interferon per $10^6$ cells.

EXAMPLE 2

Namalwa cells were cultivated in suspension in 85 liters of growth medium until they reached a cell density of $5 \times 10^5$ cells/ml. At this stage cells are in a logarithmic growth phase with a maximum of DNA synthesis. The stimulator substance was added to the cell culture medium as aqueous solution for a time span of t hours at 35.5° to 37° C. at a concentration of c m moles/l. After this pretreatment period during which the rate of DNA synthesis dropped to less than 12% of an untreated control culture and the majority of cells had accumulated in a resting phase corresponding to the G1 phase of the cell cycle, cells were pelleted by centrifugation at $700 \times g$ in a continuous flow centrifugation procedure. Cells collected in this way were resuspended at a density of $1 \times 10^7$ cells/ml in 9 liters of growth medium, which contained the stimulator substance at a concentration of c m moles/l and incubated for 4 hours at 35.5 to 37° C. together with $2^8$ hemagglutinating units of HVJ/ml in a mechanically stirred bottle. Cells, induced in this way, were collected by centrifugation, suspended in 18 liters of serum free Eagle's Minimum essential medium (with Earle's salts) at a density of $5 \times 10^6$ cells/ml and incubated at 36° C. at a pH of 7.1 for 24 hours in a 20 liter vessel with mechanical stirring.

Cellular material was removed by centrifugation ($2000 \times g$, 30 minutes), the cell supernatant representing the crude interferon preparation. It was adjusted to a pH of 2 by addition of 5 N hydrochloric acid and kept for 3 to 5 days at 4° C. for inactivation of the viral inducer.

The following table shows the increase in the yield of interferon after addition of stimulator substance hexamethylene bisacetamide at a concentration of c m moles/l.

TABLE 2.

| Concentration of Stimulator Substance c (m moles/l) | Time of Pretreatment t (hours) | IU/$10^6$ cells+ | Yield Increase Factor |
|---|---|---|---|
| (a) 0 | — | 2,400 | 1 |
| 2.5 | 72 | 10,400 | 4 |
| (b) 0 | — | 1,480 | 1 |
| 5 | 40 | 29,800 | 20 |

+ International units interferon per $10^6$ cells.

EXAMPLE 3

Namalwa cells were cultivated in suspension in 85 liters of growth medium until a density of $1 \times 10^6$ cells/ml was reached. Cells were in exponential growth phase with optimum rate of DNA synthesis. The following mixture of of stimulator substances was added as a neutral solution for 48 hours at 35.5 to 37° C.: propionic acid, 2.5 m moles/l, and hydrocortison, 1 $\mu$mol/l. The rate of DNA synthesis had decreased within 48 hours to less than 5% of an untreated control culture, and the majority of cells had accumulated in a G 1 phase like resting state. Cells were then sedimented in a continuous flow centrifugation system at $700 \times g$. Cells collected in this way were suspended at a density of $4.5 \times 10^7$ cells/ml in 2 liters of growth medium and incubated for 2 hours with $2^{10}$ hemagglutination units HVJ/ml in roller flasks at 37° C. Cells were collected thereafter, resuspended at a density of $1 \times 10^6$ cells/ml in 85 liters of serum-free medium, and incubated as suspension culture for 36 hours at a pH of 7.3 and 35.5 to 37° C. Cellular material was removed by continuous flow centrifugation ($2000 \times g$), and the cell supernatant was adjusted with 5 N hydrochloric acid to a pH of 2 at a temperature below 10° C. and kept for 3 to 5 days at 4° C. The crude interferon preparation obtained by this procedure contained 22 times more interferon than a control culture not preincubated with stimulator substances. (Control culture: 1050 IU interferon/$10^6$ cells; propionic acid + hydrocortisone treated culture: 23 200 IU interferon/$10^6$ cells).

EXAMPLE 4

In analogy to the previous examples Namalwa cells at a density of $5 \times 10^5$ cells/ml were pretreated with the stimulator substances listed below in Table 3. This pretreatment lead to an increase in interferon yield by a factor X as compared to unpretreated control cultures:

TABLE 3.

| Stimulator Substance | Concentration c (m moles/l) | Increase in Interferon Yield Factor X |
|---|---|---|
| (a) propionic acid | 1 | 4 |
| (b) n butyric acid | 1 | 29 |
| (c) valeric acid | 1 | 4 |
| (d) propionic acid | 2.5 | 8 |
| (e) propionic acid | 5 | 31 |
| (f) n-butyric acid | 5 | 29 |
| (g) valeric acid | 5 | 22 |
| (h) caproic acid | 5 | 8 |
| (i) dimethyl sulfoxide | 140 | 4 |
| (j) dimethyl sulfoxide | 280 | 16 |

EXAMPLE 5

In analogy to the previous examples Namalwa cells at a density of $5 \times 10^5$ cells/ml were pretreated with the stimulator substances listed below in Table 4. These lead to an increase in interferon yield by a factor X as compared to unpretreated control cultures:

TABLE 4.

| Stimulator Substance | Concentration c ($\mu$ moles/l) | Increase in interferon Yield factor X |
|---|---|---|
| (a) Prednisolone | 10 | 36 |
|  | 1 | 40 |
|  | 0.1 | 6 |
| (b) Dexamethasone | 10 | 44 |

TABLE 4.-continued

| Stimulator Substance | Concentration c (μ moles/l) | Increase in interferon Yield factor X |
|---|---|---|
| | 1 | 29 |
| | 0.1 | 31 |
| | 0.01 | 14 |
| (c) Triamcinolone | 10 | 19 |
| | 1 | 16 |
| | 0.1 | 12 |
| (d) Hydrocortisone | 10 | 50 |
| | 1 | 17 |
| | 0.1 | 12 |
| (e) Cortexolone | 10 | 4 |
| (f) Prednisone | 10 | 3.5 |

SEPARATION AND PURIFICATION

Crude interferon prepared according to Examples 1 to 5 can be separated and/or purified according to, for example, the following procedure:

(a) Concentration by zinc acetate precipitation

An amount of 17.2 liters of crude interferon were neutralized with 2 N sodium hydroxide and a 1 mol/l solution of zinc acetate added under constant stirring to a final concentration of 0.02 mol/l. The pH value was titrated to 7.2 by addition of sodium hydroxide. The formed precipitate containing the interferon activity was allowed to settle for two hours, and the supernatant was removed by suction. The sediment was pelleted by centrifugation and redissolved in 640 ml of 0.1 N hydrochloric acid. The pH value was adjusted to 2.5. The turbid solution was clarified by centrifugation (2000×g, 60 minutes).

(b) First chromatography on the ion exchanger

Six hundred and fifty-three millimeters of acid interferon solution were mixed with 25.8 g of SP-Sephadex C-25 (Pharmacia Fine Chemicals, Uppsala, Sweden), and the mixture was stirred overnight at 0° to 4° C. During this procedure interferon was adsorbed by the ion exchanger, which was then washed according to the following procedure:

Three times with 1 liter of 0.1 mol/l glycine/hydrochloric acid buffer at a pH of 2.5; three times with 1 liter of 0.1 mol/l solution of potassium citrate at a pH of 4.0 and containing 0.005 mol/l of disodium ethylenediaminetetraacetate.

Washing was carried on until no zinc ions can be detected with dithizone in the decanted washings. The ion exchanger was then suspended in citrate buffer and transferred to a chromatographic column. Interferon was eluted with a buffer containing 0.1 mol/l of potassium phosphate and 1 mol/l of potassium chloride and having a+pH of 8. Fractions containing protein were collected (210 ml) using extinction at 280 nm ($E_{280}$ nm) as indicator for protein.

(c) Concentration with potassium thiocyanate

The pooled fractions (210 ml) were adjusted with hydrochloric acid to a pH of 3.5 at 4° C. and the solution was clarified by centrifugation. To the clarified solution 1/10 of the volume of a solution of 10 mol/l of potassium-thiocyanate was added. The resulting precipitate containing the interferon activity was allowed to settle, collected by centrifugation, and resuspended in 3 ml of 0.1 mol/l solution of potassium phosphate buffer having a pH of 8. The solution was clarified by ultracentrifugation (70,000×g, 80 minutes).

(d) Gelfiltration

Sephadex G-100 (particle size 40–120μ; Pharmacia Fine Chemicals, Uppsala, Sweden) was equilibrated in phosphate buffered saline (PBS) containing 0.001 mol/l of disodium ethylenediaminotetraacetate and transferred to a chromatographic column (5×50 cm). Chromatography was carried out at 4° C. with the equilibration buffer at a flow rate of 40 ml/hour. Each freshly prepared column had been standardized before use with proteins of known molecular weight. The concentrated interferon preparation (3.5 ml) was fractionated according to the molecular weight, and the fractions corresponding to a molecular weight between 10,000 and 35,000 Daltons were pooled (30.5 ml). In this range the entire interferon activity eluted (molecular weight of 22,000).

(e) Second ion exchange chromatography

The pooled fractions (30.5 ml) were adjusted with hydrochloric acid to a pH of 3 and applied to a 1×7 cm column SP-Sephadex C 25 which had been equilibrated with a solution containing a 0.1 mol/l of potassium citrate and having a pH of 3. Interferon was adsorbed under these conditions. After a short washing with citrate buffer interferon was eluted with a solution of 0.1 mol/l of potassium phosphate having a pH of 8. The fractions of the eluate which contained protein (determined by $E_{280}$ nm absorbancy) were collected, dialized against PBS, and stored at −20° C. The volume of the purified concentrate was 3.9 ml.

We claim:

1. A process for the preparation of human interferon, which comprises the steps of (1) adding to a permanent cell line of lymphoid origin a stimulator substance selected from the group consisting of N,N'-diacetylated alkylene-α,ω-diamines of 4 to 8 carbon atoms in the alkylene moiety, dimethylsulfoxide, 11 β-substituted glucocorticoids where the substituent is halogen, hydroxyl or hydroxymethyl, and mixtures thereof; (2) at least 12 hours thereafter incubating the resulting mixture with a viral interferon inducer; and (3) recovering the interferon produced thereby.

2. A process of claim 1, wherein the permanent cell line of lymphoid origin is Namalva cells.

3. A process of claim 1, wherein the stimulator substance is selected from the group consisting of pentamethylene bisacetamide, hexamethylene bisacetamide, heptamethylene bisacetamide, dimethylsulfoxide, prednisolone, dexamethasone, triamcinolone, hydrocortisone, cortexolone, prednisone and mixtures thereof, and the cells are exposed to the stimulator substance for a period of 6 to 72 hours.

4. A process of claim 3, wherein the cells are exposed to the stimulator substance for a period of from 24 to 48 hours.

5. A process of claim 1, wherein the final concentration of stimulator substance is from 0.01 μmoles/liter to 300 mmoles/liter.

6. A process of claim 1, wherein the stimulator substance is selected from the group consisting of N,N'-diacetylated alkylene-α,ω-diamines of 4 to 8 carbon atoms in the alkylene moiety, dimethylsulfoxide, and mixtures thereof, and the final concentration of the stimulator substance in the cell culture medium is from 0.1 μmoles/liter to 250 mmoles/liter.

* * * * *